US005589175A

United States Patent [19]

Vahlne et al.

[11] Patent Number: 5,589,175

[45] Date of Patent: Dec. 31, 1996

[54] PEPTIDES FOR INDUCTION OF NEUTRALIZING ANTIBODIES AGAINST HUMAN IMMUNODEFICIENCY VIRUS

[75] Inventors: Anders Vahlne, Hovas; Bo Svennerholm, Goteborg; Lars Rymo, Hovas; Stig Jeansson; Peter Horal, both of Goteborg, all of Sweden

[73] Assignee: Syntello Vaccine Development KB, Goteborg, Sweden

[21] Appl. No.: 410,384

[22] Filed: Mar. 27, 1995

Related U.S. Application Data

[63] Continuation of Ser. No. 8,092, Jan. 22, 1993, abandoned, which is a continuation of Ser. No. 589,422, Sep. 27, 1990, abandoned.

[51] Int. Cl.[6] .......................... A61K 39/21; A61K 39/12; A61K 38/14; C07K 5/00

[52] U.S. Cl. .................................... 424/208.1; 424/184.1; 424/188.1; 424/204.1; 530/324

[58] Field of Search ......................... 530/324; 424/188.1, 424/204.1, 184.1

[56] References Cited

U.S. PATENT DOCUMENTS

| | | | |
|---|---|---|---|
| 4,943,628 | 7/1990 | Rosen et al. | 530/326 |
| 5,019,387 | 5/1991 | Haynes et al. | 424/89 |

FOREIGN PATENT DOCUMENTS

| | | | |
|---|---|---|---|
| 0330359 | 8/1989 | European Pat. Off. | C07K 7/08 |
| 8602383 | 4/1986 | WIPO | C12P 21/00 |
| 8707616 | 12/1987 | WIPO | C07K 7/08 |
| WO8905820 | 6/1989 | WIPO | A61K 39/21 |
| 8910416 | 11/1989 | WIPO | C12Q 1/70 |
| 9221377 | 12/1992 | WIPO . | |

OTHER PUBLICATIONS

Haynes, 1993, "Scientific and Social issues . . . " Science 260:1279–1286.

Fox, 1994, "No Winners against AIDS" Biotechnology 12: 128.

A. Vahlne, et al. "Immunisation of Monkeys With Synthetic Peptides Disclose Conserved Areas on gp120 of Human Immunodeficiency Virus Type 1 Associated with Cross–Neutralizing Antibodies and T-cell Recognition", Proceedings of The National Academy of Sciences, vol. 88, No. 23, Dec. 1, 1991, pp. 10744–10748.

D. F. Nixon, et al. "Cellular and Humoral Antigenic Epitopes in HIV and SIV", Immunology, vol. 76, No. 4, Aug. 1992, pp. 515–534.

Chanh, et al., 1986 "Induction of anti–HIV Neutralizing Antibodies by Synthetic Peptides". EMBOJ 5(11):3065–3071.

Dreesman, 1988 "Experimental Gp 120 and Gp 41 AIDS Vaccines" Meeting Abstract, 7th Summer Symposium in Mol. Biol. . . . Jul. 27–29, 1988 University Park, PA. p. 42.

Allan et al., "Major Glycoprotein Antigens that Induce Antibodies in AIDs Patients Are Encoded by HTLV–III", Science, 228:1091–1094 (1985).

Barin et al., "Virus Envelope Protein of HTLV–III Represents Major Target Antigen for Antibodies in AIDs Patients", Science, 228:1094–1096 (1985).

Cabradilla et al., "Serodiagnosis of Antibodies to the Human AIDs Retrovirus With a Bacterially Synthesized env Polypeptide", Biotechnology, 4:128:133 (1986).

Chang et al., "Detection of Antibodies to Human T–Cell Lymphotrophic Virus III (HTLV–III) With an Immunoassay Employing a Recombinant *Escherichia coli*—Derived Viral Antigenic Peptide", Biotechnology, 3:905–909 (1985).

Kennedy et al., "Antiserum to a Synthetic Peptide Recognizes the HTLV–III Envelope Glycoprotein", Science, 231:1556–1559 (1986).

Lerner et al., "In, The Biology of Immunological Disease: A Hospital Practice Book", (Dixon and Fisher eds.) pp. 331–338 (1983).

Lerner, "Antibodies of Predetermined Specificity in Biology and Medicine", Adv. Immunol., 36:1–44 (1984).

Van Regenmortel, "Synthetic Peptides as Viral Vaccines", Ann. Inst. Pasteur/Virol. 137E:497–528 (1986).

Erickson and Merrifield in: The Proteins, 3rd Ed. vol. 2, Academic Press, N.Y., Chapter 3 pp. 255–527 (1976).

Cianciolo et al., "Macrophage Accumulation in Mice is Inhibited by Low Molecular Weight Products from Murine Leukemia Viruses", J. Immunol., 124–2900–2905 (1980).

Cianciolo et al., "Inhibition of Lymphocyte Proliferation by a Synthetic Peptide Homologous to Retroviral Envelope Proteins", Science, 230:453–455, (1985).

Steward et al., "Synthetic Peptides: A Next Generation of Vaccines?", Immunol. Today, 8:51–58 (1987).

Berman et al., "Protection of Chimpanzees from Infection by HIV–1 after Vaccination With Recombinant Glycoprotein gp120 but Not gp160", Nature 345:622–625 (1990).

Bolognesi, "HIV Antibodies and Vaccine Design", AIDS 1989 3:S111–S118.

Muesing et al., "Nucleic Acid Structure and Expression of the Human AIDs/Lymphadenopathy Retrovirus", Nature, 313:450–458, (1985).

Sanchez et al., "Recombinant System for Overexpression of Cholera Toxin B Subunit In *Vibrio cholerae* as a Basis For Vaccine Development", Proc. Natl. Acad Sci USA, 86:481–485 (1989).

Takahashi et al., "Induction of $CD8^+$ Cytotoxic T Cells by Immunization With Purified HIV–1 Envelope Protein In ISCOMs", Nature, 344:873–875 (1990).

(List continued on next page.)

*Primary Examiner*—Lynette F. Smith
*Attorney, Agent, or Firm*—Knobbe, Martens Olson & Bear

[57] ABSTRACT

In accordance with the present invention, novel peptides corresponding to epitopes of human immunodeficiency virus-1 gp120 protein and analogues and homologs thereof are provided. These peptides can be utilized alone or in combination, uncoupled or coupled to other molecules or substrates. The peptides are useful in immunization against human immunodeficiency virus infection and in production of polyclonal and monoclonal antibodies.

8 Claims, No Drawings

OTHER PUBLICATIONS

Bergot et al., "Utility of Trifluromethane Sulfonic Acid as a Cleavage Reagent in Solid Phase Peptide Synthesis", Applied Biosystems User Bulletin, Peptide Synthesizer, Issue No. 16, Sep. 2, 1986.

Jeansson et al., "Elimination of Mycoplasmas from Cell Cultures Utilizing Hyperimmune Sera", Ex. Cell Res., 161:181–188 (1985).

Ho et al., Science, 239:1021–1023 (1988).

Neurath, et al., 1990, "B Cell Epitope Mapping of Human, . . . " J. General Virology 71:85–95.

Modrow et al., 1989, "Use of Synthetic Oligopeptides in Identification . . . " J. Acquired Immune Deficiency Syndrome 2:21–27.

Brown, "AIDS Vaccine Trials Viewed With Caution" The Washington Post Newspaper Jun. 10, 1993.

Ed. Dani bolognesi, "Hiv binding to the CD4 molecule: conformation dependence and binding inhibition studies", J. S. Mc Dougal et al., 1988, Human Retroviruses, Cancer and AIDS, pp. 269–281.

Chemical Abstracts, vol. 111, No. 7, 14 Aug. 1989, (Columbus, Ohio, US), Palker, Thomas J et al.: "Polyvalent hyman immunodeficiency virus synthetic immunogen comprised of envelope gp120 T helper cell sites and B cell neutralization epitopes", see p. 553.

Cohen, 1993, "Jitters Jeopardize AIDS Vaccine Trials" Science 262: 980–981.

PEPTIDES FOR INDUCTION OF NEUTRALIZING ANTIBODIES AGAINST HUMAN IMMUNODEFICIENCY VIRUS

This application is a continuation of application Ser. No. 08/008,092, filed Jan. 22, 1993 now abandoned; which is a continuation of application Ser. No. 07/589,422, filed Sep. 27, 1990 now abandoned.

BACKGROUND OF THE INVENTION

The present invention relates to peptides suitable for use in vaccination against AIDS.

The human immunodeficiency virus (HIV) is responsible for the disease that has come to be known as acquired immune deficiency syndrome (AIDS). Although initially recognized in 1981, no cure has yet been found for this inevitably fatal disease. HIV is spread by a variety of means such as sexual contact, infected blood or blood products and perinatally. Due to the complexity of HIV infection and the paucity of effective therapies, eradication of AIDS will most likely occur by preventing new infections rather than curing those persons already infected. To this end a great deal of effort has been expended in developing methods for detecting and preventing infection. Diagnostic procedures have been developed for identifying infected persons, blood and other biological products.

Like most viruses, HIV often elicits the production of neutralizing antibodies, unlike many other viruses and other infectious agents for which infection leads to protective immunity, however, HIV specific antibodies are insufficient to halt the progression of the disease. Therefore, in the case of HIV, a vaccine that elicits the immunity of natural infection could prove to be ineffective. In fact, vaccines prepared from the HIV protein gp160 appear to provide little immunity to HIV infection although they elicit neutralizing antibodies. The failure to produce an effective anti-HIV vaccine has led to the prediction that an effective vaccine will not be available until the end of the 1990's.

The HIV genome has been well characterized. Its approximately 10Kb encode sequences that contain regulatory segments for HIV replication as well as the gag, pol and env genes coding for the core proteins, the reverse transcriptase-protease-endonuclease, and the internal and external envelope glycoproteins respectively.

The HIV env gene encodes the intracellular glycoprotein, gp160, which is normally processed by proteolytic cleavage to form gp120, the external viral glycoprotein, and gp41, the viral transmembrane glycoprotein. The gp120 remains associated with HIV virions by virtue of noncovalent interactions with gp41. These noncovalent interactions are weak, consequently most of the gp120 is released from cells and virions in a soluble form.

Previous studies have shown that the proteins encoded by the gag and especially the env regions of the HIV-1 genome are immunogenic since antibodies to the products of the gag and env genes are found in the sera of HIV infected, AIDS and ARC ("AIDS Related Condition") patients.

It has previously been shown that some antibodies obtained from sera of AIDS and ARC patients, as well as asymptomatic individuals infected with the virus are specific to gp120 and gp160. Occasionally these antibodies, are neutralizing. The envelope glycoproteins are the HIV-1 antigen most consistently recognized by antibodies in AIDS and ARC patient sera. Allan et al., "Major Glycoprotein Antigens that Induce Antibodies in AIDS Patients are Encoded by HTLV-III", Science, 228:1091–1094 (1985); and Barin et al., "Virus Envelope Protein of HTLV-III Represents Major Target Antigen for Antibodies in AIDS Patients", Science, 228:1094–1096 (1985). In addition, antibodies in patient sera also recognize epitopes of the viral core proteins encoded by the gag gene.

Immunologically important HIV-1 antigens for use in diagnosis and as potential vaccine compositions have been prepared by cloning portions of the HIV-1 genome in various expression systems such as bacteria, yeast or vaccinia. Cabradilla et al., "Serodiagnosis of Antibodies to the Human AIDs Retrovirus With a Bacterially Synthesized env Polypeptide", Biotechnology, 4:128–133 (1986); and Chang et al., "Detection of Antibodies to Human T-Cell Lymphotropic Virus-III (HTLV-III) With an Immunoassay Employing a Recombinant *Escherichia coli*—Derived Viral Antigenic Peptide", Biotechnology, 3:905–909 (1985). HIV-1 antigens produced by recombinant DNA methods, however, must still be exhaustively purified to avoid adverse reactions upon vaccination and false positive reactions in ELISA assays due to any antibody reactivity to antigens of the expression system which may contaminate the HIV-1 antigen preparation. Also, denaturation of HIV-1 antigens during purification may destroy important antigen activity. Preparation of proteins from intact viruses can also result in contamination by intact virus.

Several publications have presented data showing immunologic reactivity of selected synthetic peptides corresponding to antigenic proteins of HIV-1. In one study, a peptide having the amino acid sequence Tyr-Asp-Arg-Pro-Glu-Gly-Ile-Glu-Glu-Glu-Gly-Gly-Glu-Arg-Asp-Arg-Asp-Arg-Ser-Gly-Cys which corresponds to amino acid residues 735–752 of HIV-1 was synthesized. Kennedy et al., "Antiserum to a Synthetic Peptide Recognizes the HTLV-III Envelope Glycoprotein", Science, 231:1556–1559 (1986). This peptide, derived from a portion of gp41, was used to immunize rabbits in an attempt to elicit a neutralizing antibody response to HIV-1. Furthermore, several sera from AIDS patients known to contain anti-gp41 antibodies were weakly reactive with this peptide, thus indicating that this peptide contains at least one epitope recognized, to some extent, by antibodies to native gp160/gp41. However, this peptide has not been shown to elicit neutralizing antibodies in mammals other than rabbits nor has it been suggested for use as a human vaccine.

SUMMARY OF THE INVENTION

In accordance with the present invention, novel peptides corresponding to epitopes of HIV-1 gp120 protein and analogues and homologs thereof are provided. These peptides can be utilized alone or in combination, uncoupled or coupled to other molecules or substrates. The peptides are useful in immunization against HIV infection, induction of a heightened immune response to HIV and in production of polyclonal and monoclonal antibodies.

DETAILED DESCRIPTION OF THE INVENTION

The present invention provides peptides which have been found to elicit production of HIV neutralizing antibodies by primate subjects. The peptides correspond to regions of the gp120 protein with coordinates as defined by Kennedy et al. (1986). The peptides of the present invention are termed gp120-12 (amino acid coordinates 159–183), gp120-15 (amino acid coordinates 200–225), gp120-16 (amino acid coordinates 213–237) and gp120-19 (amino acid coordinates 255–276). Although peptide gp120-19 is similar to a peptide that has been described (Ho et al., "Second conserved Domain of gp120 is Important for HIV Infectivity and Antibody Neutralization", Science, 239:1021–1023 (1988)), it has now been found that gp120-19 elicits neutralizing antibodies in primates. The peptides of the present invention can be used as immunogens in vaccine compositions and to elicit polyclonal or monoclonal antibody production; particularly important are HIV neutralizing antibodies.

Proteins contain a number of antigenic determinants or epitopes which are the regions of the proteins comprising the recognition and binding sites for specific antibodies. In general, proteins contain between 5 to 10 epitopes, each of which contains a sequence of 6 to 8 amino acids. Epitopes can be either continuous, in which the 6 to 8 amino acids are present in linear sequence, or discontinuous, in which the amino acids that form the epitope are brought together by the three dimensional folding of the protein. Even though an epitope constitutes only a relatively few amino acids, its reactivity with an antibody may be influenced by the amino acids in the protein which surround the epitope.

Studies aimed at mapping antigenic sites or epitopes of proteins have been aided by the use of synthetic peptides corresponding to various regions of the proteins of interest. Lerner et al., in, The Biology of Immunological Disease: A Hospital Practice Book, (Dixon and Fisher, eds.) pp. 331–338 (1983); and Lerner, "Antibodies of Predetermined Specificity in Biology and Medicine", Adv. Immunol., 36:1 44 (1984). In addition to their usefulness in epitope mapping studies, synthetic peptides, if encompassing major antigenic determinants of a protein, have potential as vaccines and diagnostic reagents. Van Regenmortel, "Synthetic Peptides as Viral Vaccines Ann. Inst. Pasteur/Virol. 137E:497–528 (1986); and Van Regenmortel, Laboratory Techniques in Biochemistry and Molecular Biology, Buroden and Van Knippenburg eds. Vol. 19, Synthetic Peptides as Antigens, Elsevier ISBN 0-444-80974-0 (1988).

Synthetic peptides have several advantages with regard to specific antibody production and reactivity. The exact sequence of the synthesized peptide can be selected from the amino acid sequence of the protein as determined by amino acid sequencing of the protein or the predicted amino acid sequence determined from the DNA sequence encoding the protein. The use of specific synthetic peptides eliminates the need for the full-length protein in vaccination and the production of or assay for antibodies. Furthermore, the solid phase peptide synthetic techniques of Merrifield and coworkers allow for essentially unlimited quantities of the synthesized peptide of interest to be chemically produced. Erickson and Merrifield In: The Proteins, 3rd Edit., Vol. 2, Academic Press, New York, Chapter 3 pp. 255–527 (1976). The availability of automated peptide synthesizers has further advanced such techniques.

Although a variety of criteria can be used to predict antigenic regions of proteins, peptides corresponding to such regions may not always be useful as vaccines. For example, antigenicity may be lost because the peptide is not in the proper spatial orientation to be recognized by antibodies which react with the protein. It has also been found that certain peptides derived from type C retroviruses and HIV act as immune-suppressive agents much as HIV itself. Cianciolo et al., "Macrophage Accumulation in Mice is Inhibited by Low Molecular Weight Products from Leukemia Viruses", J. Immunol., 124:2900–2905 (1980); and Cianciolo et al., "Inhibition of Lymphocyte Proliferation by a Synthetic Peptide Homologous to Retroviral Envelope Proteins", Science, 230:453–455 (1985). Peptides such as these, which have a deleterious effect on the patient, would not be suitable for use as vaccines.

Furthermore, as is particularly evident with HIV-1 and HIV-2, there is significant genetic variability within each of these two virus groups leading to many serotypes, or isolates, of the viruses. This has put a significant constraint on choosing a region of a protein from which to derive a peptide for use in formulating immunogens. However, certain immunodominant portions of HIV-1 and HIV-2 proteins have been found to be relatively invariant. Synthetic peptides may also be key to viral vaccines in that they may induce an immune response against type common sequences not normally immunogenic in the native molecule. These otherwise silent epitopes may be of broad protective specificity. Steward et al., "Synthetic Peptides: A Next Generation of Vaccines", Immunol. Today, 8:51–58 (1987). Several experimental vaccines have been formulated with the aim of preventing infection in those people who are likely to be exposed to the virus. Berman et al., "Protection of Chimpanzees from Infection by HIV-1 After Vaccination With Recombinant Glycoprotein gp120 but Not gp160", Nature, 345:622–625 (1990).

Synthetic peptides corresponding to regions of immunologically important proteins of HIV have now found immediate use in diagnostic methods for detection of HIV, as potential vaccines for HIV and for the production of polyclonal and monoclonal antibodies.

A number of neutralization epitopes on gp120 have been found and defined by several investigators, for an overview see Bolognesi, HIV Antibodies and Vaccine Design AIDs 1989 3 (1):S111–S118. In his overview Bolognesi refers to four different virus neutralization epitopes with the following amino acid coordinates: 254–274, 303–337, 458–484 and 491–523. The peptide with amino acid coordinates 254–274 was used to immunize rabbits and the resulting antiserum was found to neutralize HIV-1 as described above. Ho et al. (1988).

The peptides encompassed by the invention comprise amino acid sequences each containing at least one continuous (linear) epitope that elicits production of HIV specific antibodies in the immunized host.

The invention thus encompasses immunogenic peptides corresponding to regions of HIV gp120 protein encoded by the envelope gene of HIV-1 HTLV III-B described by Muesing et al., "Nucleic Acid Structure and Expression of the Human AIDs/Lymphadenopathy Retrovirus", Nature, 313:450–458 (1985). The nucleotide sequence is given in Genbank Release 63 under the name HIVPV22. The invention further encompasses functionally equivalent variants of the peptides which do not significantly affect the immunogenic properties of the peptides. For instance, conservative substitution of amino acid residues, one or a few amino acid deletions or additions, and substitution of amino acid residues by amino acid analogues are within the scope of the invention.

Homologs are peptides which have conservatively substituted amino acid residues. Amino acids which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Homologous peptides are considered to be within the scope of the invention if they are recognized by antibodies which recognize the peptides designated gp120-12, gp120-15, gp120-16 and gp120-19 the sequences of which are shown below. Further, all homologous peptides corresponding to the peptides of the present invention but derived from different HIV isolates are also encompassed by the scope of this invention.

Analogues are defined as peptides which are functionally equivalent to the peptides of the present invention but which contain certain non-naturally occurring or modified amino acid residues. Additionally, polymers of one or more of the peptides, and peptide analogues or homologs are within the scope of the invention. Also within the scope of this invention are peptides of fewer amino acid residues than gp120-12, gp120-15, gp120-16 and gp120-19, respectively, but which encompass one or more immunogenic epitopes present in any one of the peptides and thus retain the immunogenic properties of the base peptide.

The peptides were synthesized by known solid phase peptide synthesis techniques. Barany and Merrifield, The Peptides: Analysis, Synthesis, Biology, Vol. 1, Gross and Meinenhofer, eds., Academic Press, New York, Chap. 1 (1980). The synthesis also allows for one or more amino acids not corresponding to the original protein sequence to be added to the amino or carboxyl terminus of the peptide. Such extra amino acids are useful for coupling the peptides to another peptide, to a large carrier protein or to a solid support. Amino acids that are useful for these purposes include but are not limited to tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptides to another protein or peptide molecule or to a support. Procedures for coupling peptides to each other, carrier proteins and solid supports are well known in the art. Peptides containing the above-mentioned extra amino acid residues either carboxy or amino terminally, uncoupled or coupled to a carrier or solid support are consequently within the scope of the invention. Reference to the peptides of the present invention encompasses all of the embodiments discussed herein.

An alternative method of vaccine production is to use molecular biology techniques to produce a fusion protein containing one or more of the peptides of the present invention and a highly immunogenic protein. For instance, fusion proteins containing the antigen of interest and the B subunit of cholera toxin have been shown to induce an immune response to the antigen of interest. Sanchez et al., "Recombinant System For Overexpression of Cholera Toxin B Subunit In Vibrio cholerae as a Basis for Vaccine Development", Proc. Natl. Acad. Sci. USA, 86:481–485 (1989).

The novel peptide sequences are set forth below. The amino acid residues are derived from the nucleotide sequence previously described by Muesing et al., "Nucleic Acid Structure and Expression of the Human AIDS/Lymphadenopathy Retrovirus", Nature, 313:450–458 (1985). It is preferred that the peptides possess an amido group at their carboxy termini rather than a carboxyl group. The carboxy terminus can also be a carboxyl group as well as a moiety described below.

gp120-12
X—Gly—Glu—Ile—Lys—Asn—Cys—Ser—Phe—Asn—Ile—Ser—Thr—Ser—Ile—Arg—Gly—Lys—Val—Gln—Lys—Glu—Tyr—Ala—Phe—Phe—Y—Z
gp120-15
X—Leu—Thr—Ser—Cys—Asn—Thr—Ser—Val—Ile—Thr—Gln—Ala—Cys—Pro—Lys—Val—Ser—Phe—Glu—Pro—Ile—Pro—Ile—His—Tyr—Cys—Y—Z
gp120-16
X—Pro—Lys—Val—Ser—Phe—Glu—Pro—Ile—Pro—Ile—His—Tyr—Cys—Ala—Pro—Ala—Gly—Phe—Ala—Ile—Leu—Lys—Cys—Asn—Asn—Y—Z
gp120-19
X—Thr—His—Gly—Ile—Arg—Pro—Val—Val—Ser—Thr—Gln—Leu—Leu—Leu—Asn—Gly—Ser—Leu—Ala—Glu—Glu—Glu—Y—Z wherein X is either a hydrogen atom of the amino terminal $NH_2$ group of the peptide or an additional amino acid being selected to facilitate coupling of the peptide to a carrier; Y is absent or Cys; and Z is the carboxyl group of the carboxy terminal amino acid or an amido group. The amino acid abbreviations used are defined in Table 2.

The peptides are useful as vaccines to protect against future infection by HIV or to heighten the immune response to HIV in subjects already infected by HIV. Although any human subject could be vaccinated with the peptides, the most suitable subjects are people at risk for HIV infection. Such subjects include but are not limited to homosexuals, prostitutes, intravenous drug users and those in the medical professions who have contact with patients or biological samples. The invention also provides monoclonal and polyclonal antibodies which specifically recognize the peptides. The invention further provides antibodies which neutralize HIV.

In the preferred embodiment of the present invention, the peptides are formulated into compositions for use as immunogens. These immunogens can be used as vaccines in mammals including humans or to elicit production of polyclonal and monoclonal antibodies in animals. For formulation of such compositions, an immunogenically effective amount of at least one of the peptides is admixed with a physiologically acceptable carrier suitable for administration to mammals including humans. The peptides may be covalently attached to each other, to other peptides, to a protein carrier or to other carriers, incorporated into liposomes or other such vesicles, and/or mixed with an adjuvant or adsorbent as is known in the vaccine art. For instance, the peptide or peptides can be mixed with immunostimulating complexes as described by Takahashi et al., "Induction of $CD8^+$ Cytotoxic T Cells by Immunization With Purified HIV-1 Envelope Protein in ISCOMS", Nature, 344:873–875 (1990). Alternatively, the peptides are uncoupled and merely admixed with a physiologically acceptable carrier such as normal saline or a buffering compound suitable for administration to mammals including humans.

As with all immunogenic compositions for eliciting antibodies, the immunogenically effective amounts of the peptides of the invention must be determined empirically. Factors to be considered include the immunogenicity of the native peptide, whether or not the peptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

The invention is further illustrated by the following specific examples which are not intended in any way to limit the scope of the invention.

EXAMPLE 1

Peptide Synthesis

An Applied Biosystems peptide-synthesizer Model 430 A, was utilized for the synthesis of the peptides of the present invention. Each synthesis used a p-methylbenzylhydrylamine solid phase support resin (Peptides International, Louisville, Ky.). The peptides were synthesized according to the Users Manual for Peptide Synthesizer Model 430A, Applied Biosystems, 1986.

All amino acids for use in synthesis contained t-butylcarbonyl groups (t-Boc) protecting the α-$NH_2$ group and were obtained from Novabiochem AG, Switzerland. Amino acids with reactive side chain groups contained additional protective groups to prevent unwanted and undesirable side chain reactions. The individual protected amino acids used in synthesizing all of the peptides are set forth in Table 1.

TABLE 1

| Amino Acids Used in Peptides Synthesis |
|---|
| Boc—Ala—OH |
| Boc—Arg (Tos)—OH |
| Boc—Asn—OH |
| Boc—Asp (Obzl)—OH |
| Boc—Cys (Pmeobzl)—Oh |
| Boc—Glu (Obzl)—OH |
| Boc—Gln—OH |
| Boc—Gly—OH |
| Boc—His—(Tos)—OH |
| Boc—Ile—OH˙½ $H_2O$ |
| Boc—Leu—OH˙$H_2O$ |
| Boc—Lys (2-Cl—Z)—OH (cryst.) |
| Boc—Met—OH |
| Boc—Phe—OH |
| Boc—Pro—OH |
| Boc—Ser (Bzl)—OH˙DCHA |
| Boc—Thr (Bzl)—OH |
| Boc—Trp (Formyl)—OH |
| Boc—Tyr (2-Br—Z)—OH |
| Boc—Val—OH |

Tos: Tosyl or p-Toluene sulfonic acid
Obzl = Benzyloxy
Pmeobzl = p-Methylbenzyloxy
2-CL—Z = Carbobenzoxy chloride
2-Br—Z = Carbobenzoxy bromide After completion of a particular synthesis, the protecting groups were removed from the synthesized peptide and the peptide was cleaved from the solid support resin by treatment with Trifluoromethane Sulfonic Acid (TFMSA) according to the method described by Bergot et al., "Utility of Trifluoromethane Sulfonic Acid as a Cleavage Reagent in Solid Phase Peptide Synthesis", Applied Biosystems User Bulletin, Peptide Synthesizer, Issue No. 16, Sep. 2, 1986. The following is the detailed protocol used.

1. For 1 gram peptide-resin, 3 ml Thio-Anisol 1,2-Ethane-Dithiol (2:1) was added as scavenging agent and the mixture was incubated with continuous stirring for 10 min. at room temperature.
2. Trifluoracetic Acid (TFA), 10 ml, was added and stirred continuously for 10 min. at room temperature.
3. TFMSA, 1 ml, was added dropwise with forceful stirring and reacted for 25 min. at room temperature.
4. Following cleavage, the peptides were precipitated with and washed with anhydrous ether.
5. The precipitated and washed peptides were dissolved in a small volume of TFA (approximately 5ml).
6. The dissolved peptides were again precipitated and washed as above in step 4 and the precipitate was dried under a stream of $N_2$.

Prior to use in specific assays, the peptides can be further purified, if desired, by reverse phase high performance liquid chromatography (HPLC). A particularly suitable column for such purification is the reverse-phase Vydak® C-18 column using a water (TFA)—acetonitrile (TFA) gradient to elute the peptides. Forty peptides were synthesized having the amino acid sequences shown in Table 2.

TABLE 2

| Peptide | Amino Acid Coordinates** | Amino Acid Sequence* |
|---|---|---|
| 1–28 | 7–35 | MRVKEKYQHLWRWGWRWGTMLLGMLMIC |
| 23–46 | 30–53 | GMLMICSATEKLWVTVYYGVPVWK |
| 41–64 | 48–71 | GVPVWKEATTTLFCASDAKAYDTE |
| 54–74 | 61–81 | CASDAKAYDTEVHNVWATHAC |
| 65–89 | 72–96 | VHNVWATHACVPTDPNPQEVVLVNV |
| 75–100 | 82–107 | VPTDPNPQEVVLVNVTENFNMWKNDM |
| 90–116 | 97–123 | TENFNMWKNDMVEQMHEDIISLWDQSL |
| 101–126 | 101–133 | VEQMHEDIISLWDQSLKPCVKLTPLC |
| 117–141 | 124–148 | KPCVKLTPLCVSLKCTDLKNDTNTN |
| 127–151 | 134–158 | VSLKCTDLKNDTNTNSSSGRMIMEK |
| 142–164 | 149–171 | SSSGRMIMEKGEIKNCSFNISTS |
| 152–176 | 159–183 | GEIKNCSFNISTSIRGKVQKEYAFF |
| 165–192 | 172–199 | IRGKVQKEYAFFYKLDIIPIDNDTTSYT |
| 177–205 | 184–212 | YKLDIIPIDNDTTSYTLTSCNTSVITQAC |
| 193–210 | 200–255 | LTSCNTSVITQACPKVSFEPIPIHYC |
| 206–230 | 213–237 | PKVSFEPIPIHYCAPAGFAILKCNN |
| 219–237 | 226–244 | APAGFAILKCNNKTFNGTGPCTNVSTVQC |
| 231–257 | 238–264 | KTFNGTGPCTNVSTVQCTHGIRPVVST |
| 248–269 | 255–276 | THGIRPVVSTQLLLNGSLAEEE |
| 257–282 | 265–289 | QLLLNGSLAEEEVVIRSANFTDNAK |
| 270–295 | 277–302 | VVIRSANFTDNAKTIIVQLNQSVEIN |
| 283–306 | 290–313 | TIIVQLNQSVEINCTRPNNNTRKS |
| 296–320 | 303–327 | CTRPNNNTRKSIRIQRGPGRAFVTI |
| 307–336 | 314–337 | IRIQRGPGRAFVTIGKIGNMRQAH |
| 327–343 | 328–350 | GKIGNMRQAHCNISRAKWNNTLK |
| 331–353 | 338–360 | CNISRAKWNNTLKQIDSKLREQF |
| 344–366 | 351–373 | QIDSKLREQFGNNKTIIFKQSSG |
| 354–377 | 361–384 | GNNKTIIFKQSSGGDPEIVTHSFN |
| 367–389 | 374–396 | GDPEIVTHSFNCGGEFFYCNSTQ |
| 377–400 | 385–402 | CGGEFFYCNSTQLFNSTWFNSTW |
| 390–409 | 397–416 | LFNSTWFNSTWSTEGSNNTE |
| 401–429 | 408–424 | STEGSNNTEGSDTITLP |
| 410–429 | 417–436 | GSDTITLPCRIKQFINMWQE |
| 418–444 | 425–451 | CRIKQFINMWQEVGKAMYAPPISGQIR |

TABLE 2-continued

| | | |
|---|---|---|
| 430–453 | 437–460 | VGKAMYAPPISGQIRCSSNITGLL |
| 445–466 | 452–473 | CSSNITGLLLTRDGGNNNNESE |
| 454–476 | 461–483 | LTRDGGNNNNESEIFRPGGGDMR |
| 467–488 | 474–495 | IFRPGGGDMRDNWRSELYKYKV |
| 472–499 | 484–504 | DNWRSELYKYKVVKIEPLGVA |
| 489–511 | 496–518 | VKIEPLGVAPTKAKRRVVQREKR |

*Amino acid abbreviations

| | | | | | |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic acid | Asp | D | Phenylalanine | Phe | F |
| Cysteine | Cys | C | Proline | Pro | P |
| Glutamine | Gln | Q | Serine | Ser | S |
| Glutamic acid | Glu | E | Threonine | Thr | T |
| Glycine | Gly | G | Tryptophan | Trp | W |
| Histidine | His | H | Tyrosine | Tyr | Y |
| Isoleucine | Ile | I | Valine | Val | V |

**As previously described by Muesing et al.

EXAMPLE 2

Cells and Virus Stocks

All neutralization tests were performed using H-9 cells and HTLV-111B virus (originating from R. C. Gallo and supplied by Dr. William Hall, North Shore Hospital, Manhasset, N.Y.). H-9 cells (designated H9 NY) were maintained in RPMI Medium (Gibco) supplemented with 20% fetal calf serum (FCS), Penicillin/streptomycin (PEN/STREP 50 μg/ml each and without any fungicides). Cells were subcultured at a dilution of 1:3 every 4 days.

Cells were scraped from the plates and pelleted by centrifugation at 325×g. Pelleted cells were resuspended in 1 ml of stock virus previously diluted 1/10 and allowed to adsorb for 60 min at 37° C. with frequent stirring. After adsorption of the virus, the cells were recentrifuged and resuspended in 10 ml of RPMI with 20% FCS and polybrene (2 μg/ml) (giving a final concentration of $5\times10^5$ cells/ml) and incubated at 37° C. in 5% $CO_2$.

Infected cells were shown to be detectable at 4–5 days post-infection (p.i.) by monitoring syncytia formation, positive cells in immunoflourescence and p-24 production (assayed by the Abbott p-24 antigen test). The peak of HIV production was seen 10–15 days p.i. at which time virus was collected. After low speed centrifugation to remove debris, supernatants containing virus collected from infected cells were frozen in stocks at −90° C. One virus stock with endpoint titer of 40,000 50% tissue culture infective doses ($TCID_{50}$) was used throughout the studies (referred to as NT3-NT19).

EXAMPLE 3

Preparation of Peptides for Immunization

Peptides according to the present invention were covalently coupled to ovalbumin grade V (Sigma, St. Louis, Mo., USA) at an approximate 10:1 (peptide:ovalbumin) molar ratio using N-succinimidyl 3-(2-pyridyldithio) propionate (SPDP), (Pharmacia, Uppsala, Sweden) as bifunctional linker according to the manufacturer's instructions (Pharmacia) i.e. briefly as follows;

Ovalbumin was dissolved in coupling buffer (0.2M $NaH_2PO_4$, pH8.5). The dissolved ovalbumin was then run through a Sephadex G-25M column (Pharmacia, Sweden), using the same buffer. Protein concentration was measured at 280 nm and the recovery was determined. SPDP was dissolved in 99.5% ethanol to a final concentration of 40 Mm. SPDP was then added dropwise to the ovalbumin solution under stirring. The SPDP-ovalbumin mixture was then left at room temperature for approximately 30 minutes. The ovalbumin-SPDP conjugate was separated from unconjugated SPDP by running the mixture through a Sephadex G-25M column, using water as eluent. The degree of substitution for the ovalbumin-SPDP conjugate was determined after diluting 50 μl conjugate in 2 ml of water, by measuring the diluted conjugate at 280 nm and the diluted conjugate plus 100 μl Dithiothreitol (DTT) (Sigma) at 343 nm, in order to determine the amount to be added to the peptide solution.

Finally, the synthetic peptide to be coupled to the ovalbumin-SPDP conjugate was dissolved in 10% acetic acid to a final concentration of 1 mg/ml and a suitable amount of ovalbumin-SPDP conjugate (as determined by the substitution degree above) was added and allowed to stand over night at room temperature.

EXAMPLE 4

Immunization Protocols

*Maccaca fascicularis* were used to generate antibodies. Prior to the initial peptide injection a blood sample was drawn from the monkeys. This initial blood sample is termed "pre-immune" (Tables 3–6) and is used as an internal control and analyzed simultaneously with respective immuneserum.

The monkeys were injected with 100 μg peptide-SPDP-ovalbumin suspended in 0.5 ml phosphate buffered saline (PBS). The monkeys were immunized intramuscularly three times, three weeks apart. As adjuvant, 0.5 ml of Freund's complete adjuvant was used for all immunizations. Two weeks after the final immunization the monkeys were bled and pre-immune and hyperimmune sera were subject to neutralization assays as described in Example 5.

EXAMPLE 5

HIV-1 Neutralization Assay

Sera containing antibodies that neutralize HTLV 111-B infectivity were detected by their ability to prevent HIV-1 syncytium formation, p-24 antigen production and decreased number of infected cells as determined by immunofllourescence markers, compared to control infections lacking peptide specific antisera. Stock virus, described in Example 2 was diluted to 100 $TCID_{50}$ and mixed with serial fourfold dilutions (1/5, 1/20, and 1/80) of complement-inactivated immunesera obtained from the monkeys immunized as described in Example 4. As a positive control, a guinea pig hyperimmune serum (referred to as MSV) with known HIV neutralizing titer of 1/40–1/160 was included in all experiments (kindly provided by Prof. B. Morein, Dept. Veterinary Virology, BMC, Uppsala, Sweden). After incubation for 60 min at 37° C. or 16 hours at 4° C., the serum-virus mixture was added to $1\times10^6$ H-9 cells and incubated for another 60 min at 37° C. Following incubation, the cells were washed once and placed in 24 well multidish plates with 2 ml of growth medium (RPMI, 10% FCS, 2 μg polybrene/ml) per well.

Cells were examined under the microscope (magnification ×200) for the presence of syncytia on days 5–12 p.i. Supernatants from infected cells were assayed for the presence of p-24 antigen according to the manufacturer's instructions (Abbott ag test HIVAG-1®, Enzyme Immunoassay for the Detection of Human Immunodeficiency Virus Type I (HIV-1) Antigen(s) in Human Serum or Plasma) in tenfold serial dilutions (1/10–1/1,000) at 10 days p.i. The results are presented as absorbance values at 454 nm with higher absorbance values indicating higher protein concentration and hence HIV infection. Serial dilutions of the supernatants were made so as to detect p-24 concentrations in the most accurate range (<2.0 absorbance units).

The number of infected cells were determined at the end of experiment (usually on day 15 p.i.) by acetone-fixation of cells on slides adopted for immuneflourescence (IF). An indirect IF test was used according to standard procedures described in Jeansson et al., "Elimination of Mycoplasmas from Cell Cultures Utilizing Hyperimmune Sera", Ex. Cell Res., 161:181–188 (1985), with 1/400 dilution hyperimmune sera from HIV-infected individuals and a fluorescein isothiocyanate (FITC) labeled antihuman IgG antibody (Bio-Merieux France) diluted 1/100. Tables 3–6 show the results obtained from screening of hyperimmune sera from monkeys immunized with peptides 1–40.

In Tables 3(A-D)-6 the p24 antigen content of the supernatants was analyzed by ELISA as described above. The relative amount of antigen positive cells is depicted as AG POS cells wherein the percentages are represented by: −=0%, +=>0–2%, ++=3–10% and +++=11–20% where the percentage interval indicates the number of antigen positive cells.

Table 3A (HIVNT3P1.XLS) depicts the results obtained with sera derived from monkeys immunized with peptides gp120-1–gp120-10. The cells used were H9 NY and the virus used was HTLV-IIIB, Batch 18 described in Example 2. The incubation protocol was (virus plus serum) incubation at 37° C. for one hour.

Table 3B (HIVNT4P1.XLS) depicts the results obtained with sera derived from monkeys immunized with peptides gp120-11–gp120-20. The cells used were H9 NY and the virus used was HTLV-IIIB, Batch 18 described in Example 2. The incubation protocol was (virus plus serum) incubation at 37° C. for one hour.

Table 3C (HIVNT5P1.XLS) depicts the results obtained with sera derived from monkeys immunized with peptides gp120-21–gp120-30. The cells used were H9 NY, and the virus used was HTLV-IIIB, Batch 18 described in Example 2. The incubation protocol used was virus plus serum incubated at 37° C. for one hour.

Table 3D (HIVNT6P1.XLS) depicts the results obtained with sera derived from monkeys immunized with peptides gp120-31–gp120-40. The cells used were H9 NY and the virus used was HTLV-IIIB, Batch 18 described in Example 2. The incubation protocol was (virus plus serum) incubation at 37° C. for one hour.

Table 4 (HIVTAB4.XLS) shows the results of the first retest of putative neutralizing antibodies as determined by the first test (Tables 3A–D). In each test the virus used was HITLV-IIIB, Batch 18 and the cells used were H9 NY. The First Retest results in rows 1–19 are the results of neutralization test number 5. The incubation protocol was incubation at 37° C. for one hour. The First Retest results in rows 20–32 are the results of neutralization test number 7. The incubation protocol was incubation of at 37° C. for one hour.

Table 5 (HIVTAB5.XLS) shows second, third and fourth retest results of the positive peptides. In each test the virus used was HTLV-IIIB Batch 18 and the cells used were H9 NY. The Second Retest results in rows 1–4 are the results of neutralization test number 7. The incubation protocol was incubation at 37° C. for one hour. The Second Retest results in rows 5–13 are the results of naturalization test number 12. The Third Retest results are shown rows 14–16 are the results of neutralization test number 12. The incubation protocol was incubation at 37° C. for one hour. The Fourth Retest results in rows 17–39 are the results of neutralization test number 16. The incubation protocol was at 4° C. for 16 hours. The Second Retest results in rows 40–53 are the result of neutralization test 19. The incubation protocol was cells plus virus at 4° for 16 hours.

Table 6 (HIVKOMBP.XLS) shows the neutralization assay results with combined hyperimmune sera. Note that the incubation of virus and cells was at 4° C. for 16 hours.

The results depicted in Tables 3(A-D)-6 indicate that the peptides of the present invention elicit the production of HIV neutralizing antibodies in primate subjects. The use of the peptides in vaccination of human subjects is therefore applicable to prevent infection by HIV or to induce heightened immune response in subjects already infected by HIV.

TABLE 3A

ASSAYS OF ANTISERA TO PEPTIDES gp120-1–gp120-10

| | PEPTIDE | Serum Dilution | P-24 ANTIGEN (Supernatant DIL) 1/10 | 1/100 | 1/1000 | RELATIVE AMOUNT OF AG POS CELLS |
|---|---|---|---|---|---|---|
| 1. | Pos control | | >2.0 | 1.176 | 0.158 | +++ |
| 2. | Pos control | | >2.0 | 1.194 | 0.177 | +++ |
| 3. | Pos control | | >2.0 | >2.0 | 0.464 | +++ |
| 4. | Neg control | | 0.056 | — | — | − |
| 5. | guinea pig | 1/10 | 0.178 | 0.066 | 0.063 | − |

TABLE 3A-continued

ASSAYS OF ANTISERA TO PEPTIDES gp120-1–gp120-10

| PEPTIDE | Serum Dilution | P-24 ANTIGEN (Supernatant DIL) 1/10 | 1/100 | 1/1000 | RELATIVE AMOUNT OF AG POS CELLS |
|---|---|---|---|---|---|
| 6. Pos control | 1/40 | 0.71 | 0.118 | 0.06 | ++ |
| 7. Antiserum | 1/160 | >2.0 | 0.742 | 0.11 | ++ |
| 8. | 1/320 | >2.0 | 0.484 | 0.093 | +++ |
| 9. preimmune | | ND | ND | ND | ND |
| 10. gp120-1 | 1/5 | 0.715 | 0.108 | 0.054 | ++ |
| 11. | 1/20 | >2.0 | 0.36 | 0.073 | ++ |
| 12. | 1/80 | >2.0 | 0.57 | 0.093 | ++ |
| 13. preimmune | | >2.0 | 0.437 | 0.081 | ++ |
| 14. gp120-2 | 1/5 | >2.0 | 0.86 | 0.138 | ++ |
| 15. | 1/20 | >2.0 | 0.486 | 0.093 | +++ |
| 16. | 1/80 | >2.0 | 0.257 | 0.083 | +++ |
| 17. preimmune | | >2.0 | 0.466 | 0.09 | ++ |
| 18. gp120-3 | 1/5 | >2.0 | 0.367 | 0.079 | ++ |
| 19. | 1/20 | >2.0 | 0.512 | 0.094 | ++ |
| 20. | 1/80 | >2.0 | 0.724 | 0.113 | ++ |
| 21. preimmune | | >2.0 | 0.536 | 0.094 | ++ |
| 22. gp120-4 | 1/5 | >2.0 | 0.638 | 0.092 | ++ |
| 23. | 1/20 | >2.0 | 0.448 | 0.082 | ++ |
| 24. | 1/80 | >2.0 | 0.592 | 0.097 | ++ |
| 25. preimmune | | >2.0 | 0.43 | 0.082 | ++ |
| 26. gp120-5 | 1/5 | >2.0 | 0.638 | 0.098 | ++ |
| 27. | 1/20 | >2.0 | 0.737 | 0.11 | ++ |
| 28. | 1/80 | >2.0 | 0.786 | 0.119 | +++ |
| 29. preimmune | | >2.0 | 0.822 | 0.125 | ++ |
| 30. gp120-6 | 1/5 | >2.0 | 0.716 | 0.131 | +++ |
| 31. | 1/20 | >2.0 | 0.977 | 0.119 | ++ |
| 32. | 1/80 | >2.0 | 0.861 | 0.124 | ++ |
| 33. preimmune | | >2.0 | 0.719 | 0.116 | ++ |
| 34. gp120-7 | 1/5 | >2.0 | 0.587 | 0.106 | ++ |
| 35. | 1/20 | >2.0 | 0.45 | 0.092 | ++ |
| 36. | 1/80 | >2.0 | 0.756 | 0.117 | ++ |
| 37. preimmune | | >2.0 | 0.507 | 0.096 | +++ |
| 38. gp120-8 | 1/5 | >2.0 | 0.555 | 0.098 | ++ |
| 39. | 1/20 | >2.0 | 0.59 | 0.103 | ++ |
| 40. | 1/80 | >2.0 | 0.308 | 0.081 | ++ |
| 41. preimmune | | >2.0 | 0.322 | 0.076 | +++ |
| 42. gp120-9 | 1/5 | >2.0 | 0.358 | 0.09 | ++ |
| 43. | 1/20 | >2.0 | 0.403 | 0.082 | +++ |
| 44. | 1/80 | >2.0 | 0.612 | 0.102 | +++ |
| 45. preimmune | | >2.0 | 0.747 | 0.127 | ++ |
| 46. gp120-10 | 1/5 | >2.0 | 0.3 | 0.074 | ++ |
| 47. | 1/20 | >2.0 | 0.426 | 0.092 | ++ |
| 48. | 1/80 | >2.0 | 0.442 | 0.083 | ++ |

TABLE 3B

ASSAYS OF ANTISERA TO PEPTIDES gp120-11–gp120-20

| PEPTIDE | Serum Dilution | P-24 ANTIGEN (Supernatant DIL) 1/10 | 1/100 | 1/1000 | RELATIVE AMOUNT OF AG POS CELLS |
|---|---|---|---|---|---|
| 1. preimmune | 1/5 | >2.0 | 0.882 | 0.149 | ++ |
| 2. gp120-11 | 1/5 | >2.0 | 0.73 | 0.135 | ++ |
| 3. | 1/20 | >2.0 | 1.73 | 0.299 | ++ |
| 4. | 1/80 | >2.0 | 0.700 | 0.148 | ++ |
| 5. preimmune | 1/5 | >2.0 | 1.07 | 0.151 | ++ |
| 6. gp120-12 | 1/5 | 0.157 | 0.07 | 0.076 | + |
| 7. | 1/20 | >2.0 | 1.45 | 0.22 | ++ |
| 8. | 1/80 | >2.0 | 1.37 | 0.221 | ++ |
| 9. preimmune | 1/5 | >2.0 | 0.58 | 0.107 | ++ |
| 10. gp120-13 | 1/5 | >2.0 | 1.16 | 0.194 | ++ |
| 11. | 1/20 | 1.816 | 0.37 | 0.095 | ++ |
| 12. | 1/80 | >2.0 | 1.16 | 0.187 | ++ |
| 13. preimmune | 1/5 | >2.0 | >2.0 | 0.281 | ++ |
| 14. gp120-14 | 1/5 | >2.0 | 0.81 | 0.142 | ++ |
| 15. | 1/20 | >2.0 | 1.39 | 0.219 | ++ |
| 16. | 1/80 | >2.0 | 0.83 | 0.156 | ++ |
| 17. preimmune | 1/5 | >2.0 | 1.13 | 0.192 | ++ |

TABLE 3B-continued

ASSAYS OF ANTISERA TO PEPTIDES gp120-11–gp120-20

| PEPTIDE | Serum Dilution | P-24 ANTIGEN (Supernatant DIL) 1/10 | 1/100 | 1/1000 | RELATIVE AMOUNT OF AG POS CELLS |
|---|---|---|---|---|---|
| 18. gp120-15 | 1/5 | >2.0 | 1.43 | 0.243 | +++ |
| 19. | 1/20 | 0.069 | 0.05 | 0.05 | − |
| 20. | 1/80 | >2.0 | 0.57 | 0.104 | ++ |
| 21. preimmune | 1/5 | >2.0 | 1.78 | 0.303 | ++ |
| 22. gp120-16 | 1/5 | 0.26 | 0.07 | 0.056 | + |
| 23. | 1/20 | 0.067 | 0.06 | 0.054 | − |
| 24. | 1/80 | >2.0 | 0.74 | 0.132 | ++ |
| 25. preimmune | 1/5 | >2.0 | 1.13 | 0.171 | ++ |
| 26. gp120-17 | 1/5 | >2.0 | 0.76 | 0.161 | ++ |
| 27. | 1/20 | >2.0 | 1.56 | 0.285 | ++ |
| 28. | 1/80 | >2.0 | 0.7 | 0.129 | ++ |
| 29. preimmune | 1/5 | >2.0 | 1.41 | 0.177 | ++ |
| 30. gp120-18 | 1/5 | >2.0 | >2.0 | 0.339 | ++ |
| 31. | 1/20 | >2.0 | 1.36 | 0.218 | ++ |
| 32. | 1/80 | >2.0 | 1.26 | 0.199 | ++ |
| 33. preimmune | 1/5 | >2.0 | 0.39 | 0.097 | ++ |
| 34. gp120-19 | 1/5 | 0.476 | 0.1 | 0.061 | + |
| 35. | 1/20 | 1.048 | 0.18 | 0.068 | + |
| 36. | 1/80 | >2.0 | 1.62 | 0.303 | ++ |
| 37. preimmune | 1/5 | >2.0 | 1.11 | 0.189 | ++ |
| 38. gp120-20 | 1/5 | >2.0 | 1.19 | 0.182 | +++ |
| 39. | 1/20 | >2.0 | 1.47 | 0.054 | ++ |
| 40. | 1/80 | >2.0 | 1.42 | 0.264 | ++ |

TABLE 3C

ASSAY OF ANTISERA TO PEPTIDES 21–30

| PEPTIDE | Serum Dilution | P-24 ANTIGEN (Supernatant DIL) 1/10 | 1/100 | 1/1000 | RELATIVE AMOUNT OF AG POS CELLS | NO. OF SYNCYTIA/WELL Day 5 | Day 7 |
|---|---|---|---|---|---|---|---|
| 49. pos control | | >2.0 | 0.65 | 0.09 | ++ | 12 | 72 |
| 50. pos control | | 1.85 | 0.24 | 0.061 | ++ | 6 | 27 |
| 51. neg control | | 0.4 | | | | 0 | 0 |
| 52. guinea pig | 1/10 | 0.5 | 0.04 | 0.047 | − | 0 | 0 |
| 53. pos control | 1/40 | 0.05 | 0.04 | 0.04 | − | 1 | 0 |
| 54. antiserum | 1/160 | 0.04 | 0.05 | 0.043 | + | 1 | 3 |
| 55. | 1/640 | 1.07 | 0.14 | 0.056 | + | 2 | 19 |
| 56. preimmune | 1/5 | >2.0 | 1.57 | 0.275 | | 12 | 85 |
| 57. gp120-21 | 1/5 | >2.0 | 0.4 | 0.075 | ++ | 3 | 28 |
| 58. | 1/20 | 1 | 0.17 | 0.059 | | 5 | 21 |
| 59. | 1/80 | >2.0 | 0.48 | 0.089 | | 7 | 72 |
| 60. preimmune | 1/5 | >2.0 | 1.1 | 0.182 | | 3 | ND |
| 61. gp120-22 | 1/5 | >2.0 | 1.48 | 0.221 | ++ | 2 | 75 |
| 62. | 1/20 | >2.0 | 1.07 | 0.16 | | 0 | 80 |
| 63. | 1/80 | >2.0 | 0.63 | 0.087 | | 5 | 90 |
| 64. preimmune | 1/5 | >2.0 | 0.4 | 0.083 | | 4 | 52 |
| 65. gp120-23 | 1/5 | 1.97 | 0.26 | 0.067 | ND | 0 | 20 |
| 66. | 1/20 | >2.0 | 1.63 | 0.236 | | 5 | 98 |
| 67. | 1/80 | >2.0 | 0.35 | 0.084 | | 5 | >150 |
| 68. preimmune | 1/5 | >2.0 | >2.0 | 0.355 | | 2 | 49 |
| 69. gp120-24 | 1/5 | 1.95 | 0.29 | 0.067 | + | 0 | 3 |
| 70. | 1/20 | >2.0 | 0.37 | 0.081 | | 5 | 34 |
| 71. | 1/80 | 1.87 | 0.24 | 0.069 | | 3 | 48 |
| 72. preimmune | 1/5 | >2.0 | 0.83 | 0.145 | | 0 | 91 |
| 73. gp120-25 | 1/5 | >2.0 | 0.73 | 0.11 | ++ | 1 | 25 |
| 74. | 1/20 | 1.63 | 0.23 | 0.062 | | 0 | 15 |
| 75. | 1/80 | 1.88 | 0.22 | 0.064 | | 0 | 38 |
| 76. preimmune | 1/5 | >2.0 | 0.48 | 0.089 | | 0 | 79 |
| 77. gp120-26 | 1/5 | >2.0 | 0.62 | 0.101 | ++ | 3 | 91 |
| 78. | 1/20 | >2.0 | 0.34 | 0.063 | | 3 | 35 |
| 79. gp120-26 | 1/80 | 1.27 | 0.19 | 0.061 | | 0 | 21 |
| 80. preimmune | 1/5 | >2.0 | 0.66 | 0.11 | | 2 | 52 |
| 81. gp120-27 | 1/5 | >2.0 | 0.58 | 0.098 | ++ | 1 | 26 |
| 82. | 1/20 | >2.0 | 0.65 | 0.099 | | 6 | 49 |
| 83. | 1/80 | >2.0 | 0.3 | 0.062 | | 2 | 35 |
| 84. preimmune | 1/5 | >2.0 | >2.0 | 0.317 | | 7 | 31 |

TABLE 3C-continued

ASSAY OF ANTISERA TO PEPTIDES 21-30

| PEPTIDE | Serum Dilution | P-24 ANTIGEN (Supernatant DIL) 1/10 | 1/100 | 1/1000 | RELATIVE AMOUNT OF AG POS CELLS | NO. OF SYNCYTIA/WELL Day 5 | Day 7 |
|---|---|---|---|---|---|---|---|
| 85. gp120-28 | 1/5 | >2.0 | 0.39 | 0.078 | ++ | 2 | 22 |
| 86. | 1/20 | >2.0 | 0.68 | 0.105 | | 5 | 70 |
| 87. | 1/80 | 0.99 | 0.15 | 0.05 | | 3 | >150 |
| 88. preimmune | 1/5 | >2.0 | 1.29 | 0.187 | | 5 | 97 |
| 89. gp120-29 | 1/5 | >2.0 | 0.55 | 0.096 | ++ | 3 | 112 |
| 90. | 1/20 | >2.0 | 0.85 | 0.135 | | 3 | >150 |
| 91. | 1/80 | >2.0 | 0.72 | 0.113 | | 0 | 29 |
| 92. preimmune | 1/5 | >2.0 | >2.0 | 0.326 | | 10 | 130 |
| 93. gp120-30 | 1/5 | >2.0 | 0.27 | 0.073 | + | 3 | 38 |
| 94. | 1/20 | >2.0 | 1.71 | 0.24 | | 9 | 52 |
| 95. | 1/80 | >2.0 | 0.44 | 0.082 | | 6 | ND |

TABLE 3D

ASSAYS OF ANTISERA TO PEPTIDES 31-40

| PEPTIDE | Serum Dilution | P-24 ANTIGEN (Supernatant DIL) 1/10 | 1/100 | 1/1000 | RELATIVE AMOUNT OF AG POS CELLS | NO. OF SYNCYTIA/WELL Day 6 |
|---|---|---|---|---|---|---|
| 96. pos control | | 0.976 | 0.258 | 0.123 | | 6 |
| 97. pos control | | 1.836 | 0.656 | 0.185 | | 11 |
| 98. neg control | | | | | | |
| 99. guinea pig | 1/10 | 0.103 | 0.088 | 0.09 | | 0 |
| 100. pos control | 1/40 | 0.104 | 0.087 | 0.093 | | 0 |
| 101. antiserum | 1/160 | 0.749 | 0.29 | 0.1 | | 4 |
| 102. | 1/640 | 1.066 | 0.238 | 0.237 | | 7 |
| 103. preimmune | 1/5 | 0.824 | | | | |
| 104. gp120-31 | 1/5 | 1.769 | 0.675 | 0.186 | | 47 |
| 105. | 1/20 | 1.124 | 0.302 | 0.111 | | 22 |
| 106. | 1/80 | 0.978 | 0.258 | ND | | 24 |
| 107. preimmune | 1/5 | 0.883 | | | | |
| 108. gp120-32 | 1/5 | 1.163 | 0.258 | ND | | 7 |
| 109. | 1/20 | 1.482 | 0.311 | ND | | 8 |
| 110. | 1/80 | 0.996 | 0.263 | ND | | 0 |
| 111. preimmune | 1/5 | 1.76 | | | | |
| 112. gp120-33 | 1/5 | 0.84 | 0.239 | 0.156 | | 20 |
| 113. | 1/20 | 1.282 | 0.333 | 0.144 | | 16 |
| 114. | 1/80 | 0.76 | 0.207 | ND | | 17 |
| 115. preimmune | 1/5 | ND | | | | |
| 116. gp120-34 | 1/5 | 0.293 | 0.134 | 0.12 | | 18 |
| 117. | 1/20 | 1.446 | 0.391 | 0.148 | | 17 |
| 118. | 1/80 | 0.42 | 0.15 | ND | | |
| 119. preimmune | 1/5 | ND | | | | |
| 120. gp120-35 | 1/5 | 1.485 | 0.52 | 0.142 | | 10 |
| 121. | 1/20 | 1.778 | 0.873 | 0.194 | | 26 |
| 122. | 1/80 | 1.475 | 0.196 | ND | | |
| 123. preimmune | 1/5 | 1.076 | | | | |
| 124. gp120-36 | 1/5 | 0.957 | 0.26 | 0.149 | | 28 |
| 125. | 1/20 | 1.44 | 0.448 | 0.119 | | 16 |
| 126. | 1/80 | 1.148 | 0.486 | ND | | |
| 127. preimmune | 1/5 | 1.563 | | | | |
| 128. gp120-37 | 1/5 | 0.666 | 0.155 | 0.098 | | 15 |
| 129. | 1/20 | 1.143 | 0.33 | 0.129 | | 12 |
| 130. | 1/80 | 1.362 | 0.33 | ND | | |
| 131. preimmune | 1/5 | 1.364 | | | | |
| 132. gp120-38 | 1/5 | 1.386 | 0.59 | 0.114 | | 11 |
| 133. | 1/20 | 0.576 | 0.214 | 0.106 | | 17 |
| 134. | 1/80 | 1.23 | 0.329 | ND | | |
| 135. preimmune | 1/5 | 1.854 | | | | |
| 136. gp120-39 | 1/5 | 1.376 | 0.495 | 0.182 | | 28 |
| 137. | 1/20 | 0.711 | 0.296 | 0.118 | | 17 |
| 138. | 1/80 | 0.929 | 0.237 | ND | | |
| 139. preimmune | 1/5 | ND | | | | |
| 140. gp120-40 | 1/5 | 0.862 | 0.255 | 0.132 | | 13 |
| 141. | 1/20 | 0.989 | 0.273 | 0.143 | | 10 |
| 142. | 1/80 | 0.477 | 0.164 | ND | | |

TABLE 4

RETESTING OF HYPERIMMUNE SERA WITH THE CAPACITY TO NEUTRALIZE HIV

| PEPTIDE | Serum Dilution | P-24 ANTIGEN (DIL) | | | RELATIVE AMOUNT OF AG POS CELLS | NO. OF SYNCYTIA/ WELL | |
|---|---|---|---|---|---|---|---|
| First Retest | | 1/10 | 1/100 | 1/1000 | | Day 5 | Day 7 |
| 1. pos control | | >2.0 | 0.646 | 0.09 | ++ | 12 | 72 |
| 2. pos control | | 1.853 | 0.244 | 0.061 | ++ | 6 | 27 |
| 3. neg control | | 0.039 | | | | 0 | 0 |
| 4. guinea pig | 1/10 | 0.051 | 0.04 | 0.047 | – | 0 | 0 |
| 5. pos control | 1/40 | 0.052 | 0.042 | 0.04 | – | 1 | 0 |
| 6. antiserum | 1/160 | 0.042 | 0.046 | 0.043 | + | 1 | 3 |
| 7. | 1/640 | 1.067 | 0.144 | 0.056 | + | 2 | 19 |
| 8. preimmune | 1/5 | 2 | 1.326 | 0.172 | | 10 | 112 |
| 9. gp120-12 | 1/5 | 1.083 | 0.153 | 0.06 | + | 1 | 24 |
| 10. | 1/20 | 2 | 1.487 | 0.171 | | 7 | 175 |
| 11. | 1/80 | 2 | 0.463 | 0.07 | | 6 | ND |
| 12. preimmune | 1/5 | 2 | 1.991 | 0.237 | | 2 | 64 |
| 13. gp120-16 | 1/5 | 2 | 0.355 | 0.07 | + | 0 | 13 |
| 14. | 1/20 | 0.741 | 0.103 | 0.048 | | 0 | 11 |
| 15. | 1/80 | 2 | 0.32 | 0.08 | | 0 | 35 |
| 16. preimmune | 1/5 | >2.0 | 0.547 | 0.082 | | 3 | 42 |
| 17. gp120-19 | 1/5 | 0.141 | 0.062 | 0.053 | + | 0 | 6 |
| 18. | 1/20 | 1.134 | 0.164 | 0.054 | | 0 | 26 |
| 19. | 1/80 | >2.0 | 0.455 | 0.081 | | 1 | 45 |
| First Retest | | 1/5 | 1/50 | 1/500 | | Day 7 | Day 10 |
| 20. pos control | | 1.175 | 0.426 | 0.201 | | 9 | 46 |
| 21. pos control | | 1.529 | 0.401 | 0.161 | | 32 | 167 |
| 22. neg control | | | | | | | |
| 23. guinea pig | 1/10 | 0.139 | 0.165 | 0.145 | – | 0 | 0 |
| 24. pos control | 1/40 | 0.211 | 0.159 | 0.168 | – | 1 | 0 |
| 25. antiserum | 1/160 | 0.961 | 0.299 | 0.163 | ++ | 9 | 26 |
| 26. | 1/640 | 0.989 | 0.26 | 0.159 | ++ | 5 | 20 |
| 27. gp120-24 | 1/5 | 1.067 | 0.245 | 0.166 | ++ | 4 | 34 |
| 28. | 1/20 | 0.795 | 0.204 | 0.167 | ++ | 5 | 41 |
| 29. | 1/80 | 0.433 | 0.167 | | – | 15 | 80 |
| 30. gp120-25 | 1/5 | 1.237 | 0.282 | 0.155 | ++ | 19 | 144 |
| 31. | 1/20 | 1.312 | 0.373 | 0.187 | ++ | 42 | 116 |
| 32. | 1/80 | ND | ND | ND | – | ND | ND |

TABLE 5

RETESTING OF HYPERIMMUNE SERA WITH CAPACITY TO NEUTRALIZE HTLV-III

| PEPTIDE | SERUM DILUTION | P-24 ANTIGEN (Supernatant DIL) | | | *RELATIVE AMOUNT OF AG POS CELLS | NO. OF SYNCYTIA/ WELL Day 5 | Day 7 |
|---|---|---|---|---|---|---|---|
| Second Retest | | 1/5 | 1/50 | 1/500 | | | |
| 1. gp120-16 | 1/5 | ND | ND | ND | | ND | ND |
| 2. | 1/5 | 1.924 | 1.062 | 0.282 | ++ | | |
| 3. | 1/20 | 0.365 | 0.172 | 0.145 | – | 2 | 5 |
| 4. | 1/80 | 0.163 | 0.133 | | – | 0 | 0 |
| | | 1/10 | 1/100 | 1/1,000 | | | |
| Second Retest | | | | | | | |
| 5. pos control | | >2.0 | >2.0 | 1.026 | +++ | 320 | |
| 6. pos control | | >2.0 | >2.0 | 0.639 | +++ | 220 | |
| 7. pos control | | >2.0 | >2.0 | 0.866 | +++ | 290 | |
| 8. pos control | | >2.0 | >2.0 | 0.881 | +++ | | |
| 9. neg control | | 0.223 | | | – | | |
| 10. neg control | | 0.16 | | | – | | |
| 11. gp120-24 | 1/5 | >2.0 | >2.0 | 0.545 | +++ | 112 | |
| 12. | 1/20 | >2.0 | >2.0 | 0.819 | +++ | 138 | |
| 13. | 1/80 | >2.0 | >2.0 | | +++ | 230 | |
| Third Retest | | | | | | | |
| 14. gp120-16 | 1/5 | 0.122 | 0.1 | 0.115 | – | 0 | |

TABLE 5-continued

RETESTING OF HYPERIMMUNE SERA WITH CAPACITY TO NEUTRALIZE HTLV-III

| PEPTIDE | SERUM DILUTION | P-24 ANTIGEN (Supernatant DIL) | | | *RELATIVE AMOUNT OF AG POS CELLS | NO. OF SYNCYTIA/WELL Day 5 | Day 7 |
|---|---|---|---|---|---|---|---|
| 15. | 1/20 | >2.0 | 1.14 | 0.352 | ++ | 0 | |
| 16. | 1/80 | >2.0 | >2.0 | | +++ | 210 | |
| Fourth Retest | | | | | | | |
| 17. pos control | | 1.425 | 0.732 | 0.154 | ++ | 16 | |
| 18. pos control | | 1.346 | 0.672 | 0.152 | +++ | 16 | |
| 19. pos control | | 1.431 | 0.845 | 0.182 | +++ | 17 | |
| 20. pos control | | 1.414 | 0.931 | 0.251 | | | |
| 21. neg control | | 0.067 | | | – | | |
| 22. neg control | | 0.045 | | | – | | |
| 23. neg control | | 0.042 | | | – | | |
| 24. guinea pig | 1/10 | 0.044 | 0.037 | 0.029 | | 0 | |
| 25. pos control | 1/40 | 0.063 | 0.039 | 0.029 | | 0 | |
| 26. antiserum | 1/160 | 0.036 | 0.035 | 0.055 | | 0 | |
| 27. | 1/640 | 0.556 | 0.072 | 0.034 | | 1 | |
| 28. gp120-12 | 1/8 | 0.072 | 0.043 | 0.046 | | 0 | |
| 29. | 1/32 | 0.169 | 0.054 | 0.047 | | 0 | |
| 30. | 1/128 | >2.0 | 1.124 | 0.241 | | 19 | |
| 31. gp120-16 | 1/8 | 0.043 | 0.045 | 0.049 | | 0 | |
| 32. | 1/32 | 0.052 | 0.043 | 0.048 | | 0 | |
| 33. | 1/128 | 1.54 | 0.903 | 0.014 | | 4 | |
| 34. gp120-19 | 1/8 | 0.105 | 0.043 | 0.042 | | 0 | |
| 35. | 1/32 | 0.358 | 0.08 | 0.045 | | 5 | |
| 36. | 1/128 | >2.0 | 0.944 | 0.205 | | 25 | |
| 37. gp120-24 | 1/8 | >2.0 | 0.885 | 0.155 | | 2 | |
| 38. | 1/32 | >2.0 | 1.174 | 0.293 | | 15 | |
| 39. | 1/128 | 1.158 | 0.858 | 0.213 | | 11 | |
| Second Retest | | 1/5 | 1/50 | 1/500 | | | |
| 40. pos control | | 0.916 | 0.166 | 0.099 | | | 74 |
| 41. pos control | | 1.607 | 0.469 | 0.151 | | | 130 |
| 42. pos control | | >2.0 | 0.943 | 0.203 | | | 123 |
| 43. pos control | | 1.445 | 0.319 | 0.082 | | | 195 |
| 44. neg control | | 0.145 | | | | | |
| 45. neg control | | 0.328 | | | | | |
| 46. guinea pig | 1/10 | 0.09 | 0.111 | 0.075 | | | 0 |
| 47. pos control | 1/140 | 0.096 | 0.082 | 0.078 | | | 0 |
| 48. antiserum | 1/160 | 0.094 | 0.109 | 0.091 | | | 0 |
| 49. | 1/640 | 0.996 | 0.212 | 0.104 | | | 35 |
| 50. preimmune | 1/5 | >2.0 | 0.444 | 0.162 | | | 95 |
| 51. gp120-15 | 1/5 | 0.155 | 0.094 | 0.111 | | | ND |
| 52. | 1/20 | 0.152 | 0.109 | 0.158 | | | 4 |
| 53. | 1/80 | 0.176 | 0.13 | 0.207 | | | 0 |

TABLE 6

COMBINED NEUTRALIZATION EFFECTS OF SERA FROM MONKEYS

| PEPTIDE | Serum Dilution | P-24 ANTIGEN (Supernatant DIL) 1/5 | 1/50 | 1/500 | NT TITRE OF SERUM | RELATIVE AMOUNT OF AG POS CELLS | NO. OF SYNCYTIA/WELL Day 6 |
|---|---|---|---|---|---|---|---|
| 1. Pos control | | 1.4 | 0.7 | 0.154 | | ++ | 16 |
| 2. Pos control | | 1.3 | 0.7 | 0.152 | | +++ | 16 |
| 3. Pos control | | 1.4 | 0.8 | 0.182 | | | 17 |
| 4. Pos control | | 1.4 | 0.9 | 0.251 | | | |
| 5. neg control | | 0.1 | | | | – | |
| 6. neg control | | 0 | | | | – | |
| 7. neg control | | 0 | | | | – | |
| 8. guinea pig | 1/10 | 0 | 0 | 0.029 | | | 0 |
| 9. pos control | 1/40 | 0.1 | 0 | 0.029 | | | 0 |
| 10. antiserum | 1/160 | 0 | 0 | 0.055 | 160 | | 0 |
| 11. | 1/640 | 0.6 | 0.1 | 0.034 | | | 1 |
| 12. Group I | 1/8 | 0 | 0 | 0.038 | | | 1 |
| 13. gp120.mix | 1/32 | 0 | 0 | 0.041 | | | 0 |
| 14. 12 + 16 + 19 + 24 | 1/128 | 0.2 | 0.1 | 0.043 | >128 | – | 0 |
| 15. Group II | 1/8 | 0.1 | 0 | 0.046 | | | 0 |

TABLE 6-continued

COMBINED NEUTRALIZATION EFFECTS OF SERA FROM MONKEYS

| PEPTIDE | Serum Dilution | P-24 ANTIGEN (Supernatant DIL) 1/5 | 1/50 | 1/500 | NT TITRE OF SERUM | RELATIVE AMOUNT OF AG POS CELLS | NO. OF SYNCYTIA/WELL Day 6 |
|---|---|---|---|---|---|---|---|
| 16. gp120.mix | 1/32 | 0.1 | 0.1 | 0.046 | | – | 0 |
| 17. 16 + 19 | 1/128 | 0.1 | 0.2 | 0.043 | >128 | – | 0 |
| 18. Group III | 1/8 | 0 | 0 | 0.051 | | | 0 |
| 19. gp120.mix | 1/32 | 0.1 | 0.1 | 0.043 | | – | 0 |
| 20. 16 + 24 | 1/128 | 1 | 0.3 | 0.065 | 128 | ++ | 1 |
| 21. Group IV | 1/8 | 0.2 | 0 | 0.044 | | | 2 |
| 22. gp120.mix | 1/32 | 0.1 | 0 | 0.045 | | – | 1 |
| 23. 16 + 12 | 1/128 | 0.2 | 0.1 | 0.048 | >128 | – | 0 |
| 24. gp120-12 | 1/8 | 0.1 | 0 | 0.046 | | – | 0 |
| 25. | 1/32 | 0.2 | 0.1 | 0.047 | 32 | + | 0 |
| 26. | 1/128 | >3 | 1.1 | 0.241 | | | 19 |
| 27. gp120-16 | 1/8 | 0 | 0 | 0.049 | | | 0 |
| 28. | 1/32 | 0.1 | 0 | 0.048 | 32 | – | 0 |
| 29. | 1/128 | 1.5 | 0.9 | 0.138 | | – | 4 |
| 30. gp120-19 | 1/8 | 0.1 | 0 | 0.042 | | – | 0 |
| 31. | 1/32 | 0.4 | 0.1 | 0.045 | 32 | – | 5 |
| 32. | 1/128 | >3 | 0.9 | 0.205 | | ++ | 25 |
| 33. gp120-24 | 1/8 | >3 | 0.9 | 0.155 | neg | | 2 |
| 34. | 1/32 | >3 | 1.2 | 0.293 | | | 15 |
| 35. | 1/128 | 1.2 | 0.9 | 0.213 | | | 11 |

We claim:

1. A composition consisting of a peptide of the amino acid sequence: X-Gly-Glu-Ile-Lys-Asn-Cys-Ser-Phe-Asn-Ile-Ser-Thr-Ser-Ile-Arg-Gly-Lys-Val-Gln-Lys-Glu-Tyr-Ala-Phe-Phe-Y-Z in an amount effective to elicit the production of antibodies to human immunodeficiency virus in a primate, wherein X is selected from the group consisting of a hydrogen atom of the amino terminal $NH_2$ group of the peptide and an additional amino acid selected to facilitate coupling; Y is absent or cysteine and Z is selected from the group consisting of the carboxyl group of the carboxy terminal amino acid and an amido group.

2. The composition according to claim 1, wherein the antibodies neutralize human immunodeficiency virus.

3. A composition consisting of a peptide of the amino acid sequence: X-Leu-Thr-Ser-Cys-Asn-Thr-Ser-Val-Ile-Thr-Gln-Ala-Cys-Pro-Lys-Val-Ser-Phe-Glu-Pro-Ile-Pro-Ile-His-Tyr-Cys-Y-Z in an amount effective to elicit the production of antibodies to human immunodeficiency virus in a primate, wherein X is selected from the group consisting of a hydrogen atom of the amino terminal $NH_2$ group of the peptide and an additional amino acid selected to facilitate coupling; Y is absent or cysteine and Z is selected from the group consisting of the carboxyl group of the carboxy terminal amino acid and an amido group.

4. The composition according to claim 3, wherein the antibodies neutralize human immunodeficiency virus.

5. A composition comprising of a peptide of the amino acid sequence: X-Pro-Lys-Val-Ser-Phe-Glu-Pro-Ile-Pro-Ile-His-Tyr-Cys-Ala-Pro-Ala-Gly-Phe-Ala-Ile-Leu-Lys-Cys-Asn-Asn-Y-Z in an amount effective to elicit the production of antibodies to human immunodeficiency virus in a primate, wherein X is selected from the group consisting of a hydrogen atom of the amino terminal $NH_2$ group of the peptide and an additional amino acid selected to facilitate coupling; Y is absent or cysteine and Z is selected from the group consisting of the carboxyl group of the carboxy terminal amino acid and an amido group.

6. The composition according to claim 5, wherein the antibodies neutralize human immunodeficiency virus.

7. A composition consisting of at least two peptides selected from the group consisting of the following amino acid sequences:

X—Gly—Glu—Ile—Lys—Asn—Cys—Ser—Phe—Asn—Ile—Ser—Thr—Ser—Ile—Arg—Gly—Lys—Val—Gln—Lys—Glu—Tyr—Ala—Phe—Phe—Y—Z;
X—Leu—Thr—Ser—Cys—Asn—Thr—Ser—Val—Ile—Thr—Gln—Ala—Cys—Pro—Lys—Val—Ser—Phe—Glu—Pro—Ile—Pro—Ile—His—Tyr—Cys—Y—Z; and
X—Pro—Lys—Val—Ser—Phe—Glu—Pro—Ile—Pro—Ile—His—Tyr—Cys—Ala—Pro—Ala—Gly—Phe—Ala—Ile—Leu—Lys—Cys—Asn—Asn—Y—Z in amounts effective to elicit the production of antibodies to human immunodeficiency virus in a primate, wherein X is selected from the group consisting of a hydrogen atom of the amino terminal $NH_2$ group of the peptide and an additional amino acid selected to facilitate coupling; Y is absent or cysteine and Z is selected from the group consisting of the carboxyl group of the carboxy terminal amino acid and an amido group.

8. The composition according to claim 7, wherein the antibodies neutralize human immunodeficiency virus.

* * * * *